United States Patent [19]
Johansen

[11] Patent Number: 6,100,080
[45] Date of Patent: *Aug. 8, 2000

[54] METHOD FOR ENZYMATIC TREATMENT OF BIOFILM

[75] Inventor: Charlotte Johansen, Holte, Denmark

[73] Assignee: Novo Nordisk A/S, Bagsvaerd, Denmark

[ * ] Notice: This patent issued on a continued prosecution application filed under 37 CFR 1.53(d), and is subject to the twenty year patent term provisions of 35 U.S.C. 154(a)(2).

[21] Appl. No.: 08/990,829

[22] Filed: Dec. 15, 1997

[30] Foreign Application Priority Data

Dec. 18, 1996 [DK] Denmark .................. 1446/96

[51] Int. Cl.⁷ .................................. D06M 16/00
[52] U.S. Cl. ............................................. 435/264
[58] Field of Search ............................... 435/264

[56] References Cited

U.S. PATENT DOCUMENTS

| | | | |
|---|---|---|---|
| 4,150,113 | 4/1979 | Hoogendoorn et al. | 424/50 |
| 4,478,939 | 10/1984 | Adler-Nissen et al. | 435/200 |
| 4,936,994 | 6/1990 | Wiatr | 210/632 |
| 5,108,746 | 4/1992 | Rho et al. | 424/94.2 |
| 5,116,751 | 5/1992 | Shinmen et al. | 435/194 |

FOREIGN PATENT DOCUMENTS

| | | |
|---|---|---|
| 0 342 924 A2 | 11/1989 | European Pat. Off. . |
| 0590746 | 4/1994 | European Pat. Off. . |
| WO 96/06909 | 3/1996 | WIPO . |
| WO 96/10079 | 4/1996 | WIPO . |
| WO 96/33257 | 10/1996 | WIPO . |
| WO 96/36569 | 11/1996 | WIPO . |

OTHER PUBLICATIONS

Dionysius et al., "Studies on the lactoperoxidase system: reaction kinetics and antibacterial activity using two methods for hydrogen peroxide generation", Journal of Applied Bacteriology, 1992, 72, pp. 146–153.

Brisou, J.F. 1995. Biofilm, methods for enzymatic release of microorganisms. CRC Press INc., Boca Raton, Fla. pp. 141–151, 173–176.

Russell et al. J. Agric. Food Chem. 1990, vol. 38, pp. 10–13.

*Primary Examiner*—Irene Marx
*Assistant Examiner*—Vera Afremova
*Attorney, Agent, or Firm*—Steve T. Zelson, Esq.; Reza Green, Esq.

[57] ABSTRACT

A method for cleaning and disinfecting a surface at least partly covered by a biofilm layer comprising the steps of contacting the biofilm with a cleaning composition comprising one or more hydrolases, e.g. a hydrolytic enzyme produced by a strain of the fungus *Aspergillus aculeatus,* in an amount effective for either fully or partly removing or releasing the biofilm layer from the surface; and contacting the biofilm with a bactericidal disinfecting composition comprising an oxidoreductase such as an oxidase, a peroxidase or a laccase, in an amount effective for killing the living bacterial cells present in the biofilm. In particular, a disinfecting composition comprising laccase at concentration between about 0.01 to about 1000 mg protein/ml composition and an oxidation enhancer such as methyl syringate.

19 Claims, No Drawings

METHOD FOR ENZYMATIC TREATMENT OF BIOFILM

CROSS-REFERENCE TO RELATED APPLICATIONS

This application claims priority under 35 U.S.C. 119 of Danish application no. 1446/96 filed Dec. 18, 1996, the contents of which are fully incorporated herein by reference.

The present invention relates to a method for cleaning and disinfecting a surface covered by a biofilm layer; and a cleaning and/or disinfecting composition for use in the method.

BACKGROUND OF THE INVENTION

In nutrient limited ecosystems, bacteria have a marked tendency to adhere to surfaces and initiate the formation of a biofilm. A biofilm is a community of microbes, embedded in an organic polymer matrix, adhering to a surface. In nutrient limited natural and industrial ecosystems biofilm cells will predominate and cause problems as increased frictional resistence to fluids in water conduits and on ship hulls (fouling), decreased heat transfer from heat exchangers, corrosion of metallic substrata and contamination in the food and biotechnology industry. Biofilms are also a severe problem in medical science and industry acusing dental plaque, contaminated endoscopes and contact lenses, prosthetic device colonisation and biofilm formation on medical implants.

The biofilm matrix is a collection of microcolonies with water channels in between and an assortment of cells and extracellular polymers (polysaccharides, glycoproteins, proteins). Bacterial extracellular polysaccharides are composed of homo- and heteropolysaccharides of particularly glucose, fucose, mannose, galactose, fructose, pyruvate, mannuronic acid or glucuronic acid based complexes. The different bonds between the saccharides give rise to a multitude of different polysaccharides including levans, polymannans, dextrans, cellulose, amylopectin, glycogen and alginate.

Bacteria growing in biofilms are more resistant to antibiotics and disinfectants than planktonic cells and the resistance increases with the age of the biofilm. Bacterial biofilm also exhibits increased physical resistance towards desiccation, extreme temperatures or light. As mentioned, biofilm formation causes industrial, environmental and medical problems and the difficulties in cleaning and disinfection of bacterial biofilm with chemicals is a major concern in many industries. Furthermore, the trend towards milder disinfection and cleaning compositions may increase the insufficient cleaning of surfaces covered with biofilm.

The object of present invention is to provide an efficient and environmentally safe method for eliminating biofilm and living bacterial cells present on a surface.

SUMMARY OF THE INVENTION

Surprisingly, it has been found that it is possible to disinfect and eliminate biofilm present on a surface by enzymatic treatment with at least two different enzymes capable of removing/releasing the biofilm from the surface and killing the living microbial cells, respectively.

Accordingly, the present invention relates to a method for cleaning and disinfecting a surface at least partly covered by a biofilm layer, which method comprises the consecutive or simultaneous steps of
a. contacting the biofilm with a cleaning composition comprising one or more hydrolases in an amount effective for either fully or partly removing or releasing the biofilin layer from the surface; and
b. contacting the biofilm with a bactericidal disinfecting composition comprising an oxidoreductase in an amount effective for killing the living bacterial cells present in the biofilm.

In other aspects, the invention relates to a cleaning and/or disinfecting enzyme composition, and to the use of the composition for cleaning or disinfection of biofilm-covered surfaces.

The purely enzymatic method of the invention is advantageous, since it provides a very efficient cleaning and disinfection while at the same time being non-aggressive, non-hazardous, non-toxic, and environmentally-friendly.

DETAILED DESCRIPTION OF THE INVENTION

The term "cleaning", as used herein, is intended to mean fully or partly removal of undesired material, e.g. biofilm. The removal may take place by partial or complete degradation of the biofilm due to the catalytic action of enzymes.

The term "disinfecting", as used herein, is intended to mean the capability of killing living microbial cells, i.e. bacterial, fungal or yeast cells.

In the present context, the term "bactericidal" is to be understood as capable of killing bacterial cells.

The surface

The term "surface" as used herein relates to any surface which may be covered by a biofilm layer. Examples of surfaces may be any hard surface such as metal, plastics, rubber, board, glass, wood, paper, concrete, rock, marble, gypsum and ceramic materials which optionally are coated, e.g with paint, enamel etc.; or any soft surface such as fibres of any kind (yarns, textiles, vegetable fibres, rock wool, hair etc.); or porous surfaces; skin (human or animal); keratinous materials (nails etc.). The hard surface can be present in a process equipment member of a cooling tower, a water treatment plant, a dairy, a food processing plant, a chemical or pharmaceutical process plant. The porous surface can be present in a filter, e.g. a membrane filter. Accordingly, the composition and the method according to the present invention is also useful in a conventional cleaning-in-place (C-I-P) system.

The biofilm

A biofilm may comprise a vast number of different micro-organisms or may have a specific microorganism as the predominant microbe.

In a preferred embodiment of the present invention, the biofilm to be treated is dominated or characterised by undesired bacterial cells, preferably living cells selected from the bacterial genera Pseudomonas, Staphylococcus, Aeromonas, or from the family Enterobacteriaceae (including e.g. *Escherichia coli*).

The enzymes

In a preferred embodiment of the present invention, the hydrolase(s) to be used is/are selected from the group consisting of glucosidases, i.e. cellulases (endoglucanases, cellobiohydrolases, β-glucosidases), hemicellulases (xylanases, mannanases, xylan acetyl esterases)), pectinases (arabinanases, α-arabino-furanosidases, galactanases, pectin lyases, pectin methyl esterases, polygalacturonases, rhamnogalacturonan acetyl esterases, rhamnogalacturonases), amylases; proteases, and lipases.

The hydrolases to be used may be selected according to the properties, if known, of the specific biofilm which is to be removed, or a combination of several hydrolases having different enzyme activities may be used.

Examples of specific enzymes capable of biofilm degradation are: 1,2-1,3-α-D-mannan mannohydrolase, 1,3-β-D-xylanxylanohydrolase, 1,3-β-D-glucan glucanohydrolase, 1,3(1,3;1,4)-α-D-glucan 3-glucanohydrolase, 1,3(1,3;1,4)-β-D-glucan 3(4)-glucanohydrolase, 1,3-1,4-α-D-glucan 4-glucanohydrolase, 1,4-α-D-glucan glucanehydrolase, 1,4-α-D-glucan glucohydrolase, 1,4-(1,3:1,4)-β-D-glucan 4-glucanohydrolase, 1,4-β-D-glucan glucohydrolase, 1,4-β-D-xylan xylanohydrolase, 1,4-β-D-mannan mannanohydrolase, 1,5-α-L-arabinan 1,5-α-L-arabinanohydrolase, 1,4-α-D-glucan maltohydrolase, 1,6-α-D-glucan 6-glucanohydrolase, 2,6-β-fructan fructanohydrolase, α-Dextrin 6-glucanohydrolase, α-D-galactoside galactohydrolase, α-D-glucoside glucohydrolase, α-D-mannoside mannohydrolase, acyl-neuraminyl hydrolase, Aerobacter-capsular-polysaccharide galactohydrolase, β-D-fructofuranoside fructohydrolase, β-D-fucoside fucohydrolase, α-D-fructan fructohydrolase, β-D-galactoside galactohydrolase, β-D-glucoside glucohydrolase, β-D-glucuronoside, glucuronosohydrolase, β-D-mannoside mannohydrolase, β-N-acetyl-D-hexosaminide N-acetylhexosamino hydrolase, cellulose-sulfate sulfohydrolase, collagenase, dextrin 6-α-D-glucanohydrolase, glycoprotein-phosphatidylinositol phosphatidohydrolase, hyaluronate 4-glycanohydrolase, hyaluronoglucuronidase, pectin pectylhydrolase, peptidoglycan N-acetylmuramoylhydrolase, phosphatidylcholine 2-acylhydrolase, phosphatidylcholine 1-acylhydrolase, poly (1,4-α-D-galacturonide), poly(1,4-(N-acetyl-β-D-glucosaminide))-glycanohydrolase, proteases, sucrose a-glucosidase, triacylglycerol acylhydrolase, triacylglycerol protein-acylhydrolase.

A useful hydrolytic enzyme for the method of the present invention is any enzyme having proteolytic activity at the actual process conditions. Thus, the enzyme may be a proteolytic enzyme of plant origin, e.g. papain, bromelain, ficin, or of animal origin, e.g. trypsine and chymotrypsine, or of microbial origin, i.e. bacterial or fungal origin or from yeasts. It is to be understood that any mixture of various proteolytic enzyme may be applicable in the process of the invention.

In a preferred embodiment of the invention, the proteolytic enzyme is a serine-protease, a metallo-protease, or an aspartate-protease. A serine protease is an enzyme which catalyzes the hydrolysis of peptide bonds, and in which there is an essential serine residue at the active site. They are inhibited by diisopropylfluorophosphate, but in contrast to metalloproteases, are resistant to ethylene diamino tetraacetic acid (EDTA) (although they are stabilized at high temperatures by calcium ions). They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 The serine proteases usually exhibit maximum proteolytic activity in the alkaline pH range, whereas the metalloproteases and the aspartate-proteases usually exhibit maximum proteolytic activity in the neutral and the acidic pH range, respectively.

A sub-group of the serine proteases are commonly designated as subtilisins. A subtilisin is a serine protease produced by Gram-positive bacteria or fungi. The amino acid sequence of a number of subtilisins have been determined, including at least six subtilisins from Bacillus strains, namely, subtilisin 168, subtilisin BPN, subtilisin Carlsberg, subtilisin DY, subtilisin amylosacchariticus, and mesentericopeptidase, one subtilisin from an actinomycetales, thermitase from *Thermoactinomyces vulgaris,* and one fungal subtilisin, proteinase K from *Tritirachium album.* A further subgroup of the subtilisins, subtilases, have been recognised more recently. Subtilases are described as highly alkaline subtilisins and comprise enzymes such as subtilisin PB92 (MAXACAL®, Gist-Brocades Nev.), subtilisin 309(SAVINASE®, NOVO NORDISK A/S), and subtilisin 147 (ESPERASE, NOVO NORDISK A/S).

In the context of this invention, a subtilisin variant or mutated subtilisin protease means a subtilisin that has been produced by an organism which is expressing a mutant gene derived from a parent microorganism which possessed an original or parent gene and which produced a corresponding parent enzyme, the parent gene having been mutated in order to produce the mutant gene from which said mutated subtilisin protease is produced when expressed in a suitable host. These mentioned subtilisins and variants thereof constitute a preferred class of proteases which are useful in the method of the invention. An example of a useful subtilisin variant is a variant of subtilisin 309 (SAVINASE®) wherein, in position 195, glycine is substituted by phenylalanine (G195F or $^{195}$Gly to $^{195}$Phe).

Conveniently, conventional fermented commercial proteases are useful. Examples of such commercial proteases are Alcalase® (produced by submerged fermentation of a strain of *Bacillus licheniformis*), Esperase® (produced by submerged fermentation of an alkalophilic species of Bacillus), Rennilase® (produced by submerged fermentation of a non-pathogenic strain of *Mucor miehei*), Savinase® (produced by submerged fermentation of a genetically modified strain of Bacillus), e.g. the variants disclosed in the International Patent Application published as WO 92/19729, and Durazym® (a protein-engineered variant of Savinase®). All the mentioned commercial proteases are produced and sold by Novo Nordisk A/S, DK-2880 Bagsvaerd, Denmark. Other preferred serine-proteases are proteases from Nocardiopsis, Aspergillus, Rhizopus, *Bacillus alcalophilus, B. cereus, N. natto, B. vulgatus, B. mycoide,* and subtilins from Bacillus, especially proteases from the species Nocardiopsis sp. and *Nocardiopsis dassonvillei* such as those disclosed in the International Patent Application published as WO 88/03947, especially proteases from the species Nocardiopsis sp., NRRL 18262, and *Nocardiopsis dassonvillei,* NRRL 18133. Yet other preferred proteases are the serine proteases from mutants of *Bacillus subtilins* disclosed in the International Patent Application No. PCT/DK89/00002 and in the International Patent Application published as WO 91/00345, and the proteases disclosed in EP 415 296.

Another preferred class of proteases are the metalloproteases of microbial origin. Conveniently, conventional fermented commercial proteases are useful. Examples of such a commercial protease is Neutrase® (Zn) (produced by submerged fermentation of a strain of *Bacillus subtilis*), which is produced and sold by Novo Nordisk A/S, DK-2880 Bagsvaerd, Denmark.

Other useful commercial protease enzyme preparation are Bactosol® WO and Bactosol® SI, available from Sandoz AG, Basle, Switzerland; Toyozyme®, available from Toyo Boseki Co. Ltd., Japan; and Proteinase K® (produced by submerged fermentation of a strain of Bacillus sp. KSM-K16), available from Kao Corporation Ltd., Japan.

Another hydrolytic enzyme which may be useful in the method of the present invention is a microbial lipase. As such, the lipase may be selected from yeast, e.g. Candida, lipases, bacterial, e.g. Pseudomonas or Bacillus, lipases; or fungal, e.g. Humicola or Rhizomucor, lipases. More specifically, suitable lipases may be the *Rhizomucor miehei* lipase (e.g. prepared as described in EP 238 023), *Thermomyces lanuginosa* lipase e.g. prepared as described in EP 305 216 (available from Novo Nordisk under the trade name Lipolase™), *Humicola insolens* lipase, *Pseudomonas stutzeri* lipase, *Pseudomonas cepacia* lipase, *Candida antarctica* lipase A or B, or lipases from rGPL, *Absidia blakesleena, Absidia corymbifera, Fusarium solani, Fusarium oxysporum, Penicillum cyclopium, Penicillum crustosum, Penicillum expansum, Rhodotorula glutinis, Thiarosporella phaseolina, Rhizopus microsporus, Sporobolomyces shibatanus, Aureobasidium pullulans, Hansenula anomala, Geotricum penicillatum, Lactobacillus curvatus, Brochothrix thermosohata, Coprinus cinerius, Trichoderma harzanium, Trichoderma reesei, Rhizopus japonicus* or *Pseudomonas plantari*. Other examples of suitable lipases may be variants of any one of the lipases mentioned above, e.g. as described in WO 92/05249 or WO 93/11254.

Examples of amylases useful in the method of the present invention include Bacillus amylases, e.g. *Bacillus stearothermophilus* amylase, *Bacillus amyloliquefaciens* amylase, *Bacillus subtilis* amylase or *Bacillus licheniformis* amylase (e.g. as available from Novo Nordisk under the trade name Termamyl®), or Aspergillus amylases, e.g. *Aspergillus niger* or *Aspergillus oryzae* amylase. Other examples of suitable amylases may be variants of any one of the amylases mentioned above, e.g. as described in U.S. Pat. No. 5,093, 257, EP 252 666, WO 91/00353, FR 2,676,456, EP 285 123, EP 525 610, PCT/DK93/00230.

Another useful hydrolytic enzyme is a "cellulase" or "cellulolytic enzyme" which refers to an enzyme which catalyses the degradation of cellulose to glucose, cellobiose, triose and other cello-oligosaccharides. Preferably, the cellulase is an—endoglucanase, more preferably a microbial endoglucanase, especially a bacterial or fungal endoglucanase. Examples of bacterial endoglucanases are endoglucanases derived from or producible by bacteria from the group of genera consisting of Pseudomonas or *Bacillus lautus*.

The cellulase or endoglucanase may be an acid, a neutral of an alkaline cellulase or endoglucanase, i.e. exhibiting maximum cellulolytic activity in the acid, neutral of alkaline range, respectively. Accordingly, a useful cellulase or endoglucanase is an acid cellulase or endoglucanase, preferably a fungal acid cellulase or endoglucanase, more preferably a fungal acid cellulase or endoglucanse enzyme with substantial cellulolytic activity at acidic conditions which is derived from or producible by fungi from the group of genera consisting of Trichoderma, Actinomyces, Myrothecium, Aspergillus, and Botrytis.

A preferred useful acid cellulase or endoglucanase is derived from or producible by fungi from the group of species consisting of *Trichoderma viride, Trichoderma reesei, Trichoderma longibrachiatum, Myrothecium verrucaria, Aspergillus niger, Aspergillus oryzae,* and *Botrytis cinerea*.

Another useful cellulase or endoglucanase is a neutral or alkaline cellulase or endoglucanse, preferably a fungal neutral or alkaline cellulase or endoglucanse, more preferably a fungal alkaline cellulase or endoglucanase with substantial cellulolytic activity at alkaline conditions which is derived from or producible by fungi from the group of genera consisting of Aspergillus, Penicillium, Myceliophthora, Humicola, Irpex, Fusarium, Stachybotrys, Scopulariopsis, Chaetomium, Mycogone, Verticillium, Myrothecium, Papulospora, Gliocladium, Cephalosporium and Acremonium.

A preferred alkaline cellulase or endoglucanase is derived from or producible by fungi from the group of species consisting of *Humicola insolens, Fusarium oxysporum, Myceliopthora thermophile,* or Cephalosporium sp., preferably from the group of species consisting of *Humicola insolens*, DSM 1800, *Fusarium oxysporum*, DSM 2672, *Myceliopthora thermophila*, CBS 117.65, or Cephalosporium sp., RYM-202.

Examples of xylanases useful in the method of the present invention include enzymes having xylanolytic activity which are produced or producible by a strain selected from the group of species consisting of *Humicola insolens* (see e.g. WO 92/17573), *Aspergillus aculeatus* (an enzyme exhibiting xylanase activity, which enzyme is immunologically reactive with an antibody raised against a purified xylanase derived from *Aspergillus aculeatus*, CBS 101.43, see e.g. WO 94/21785), *Bacillus pumilus* (see e.g. WO 92/03540), *Bacillus stearathermophilus* (see e.g. Wo 91/18976, WO 91/10724), Bacillus sp. AC13 (especially the strain NCIMB 40482, see e.g. WO 94/01532), *Trichoderma longibrachiatum* and Chainia sp. (see e.g. EP 0 353 342 A1), *Thermoascus aurantiacus* (see e.g. U.S. Pat. No. 4,966,850), *Trichoderma harzianum* and *Trichoderma reseei* (see e.g. U.S. Pat. No. 4,725,544), *Aureobasidium pullulans* (see e.g. EP 0 373 107 A2), *Thermomyces lanuginosus* (see e.g. EP 0 456 033 A2), *Bacillus circulans* (WO 91/18978), *Aspergillus oryzae* (see e.g. SU 4610007), *Thermomonospora fusca* (see e.g. EP 0 473 545 A2), *Streptomyces lividans* (see e.g. WO 93/03155), *Streptomyces viridosporus* (see e.g. EP 496 671 A1), *Bacillus licheniformis* (see e.g. JP 9213868) and *Trichoderma longibrachiatum* [see W. J. J. van den Tweel et al.(Eds.), "Stability of Enzymes", Proceedings of an International Symposium heeld in Maastricht, The Netherlands, Nov. 22–25, 1992, Fisk, R. S. and Simpson, pp.323–328]; or from the group of genera consisting of Thermotoga (see e.g. WO 93/19171), Rhodothermus (see e.g. WO 93/08275), Dictyoglomus (see e.g. WO 92/18612) and Streptomyces (see e.g. U.S. Pat. No. 5,116,746). Other examples of suitable xylanases may be variants (derivatives or homologues) of any one of the above-mentioned enzymes having xylanolytic activity.

A useful pectinase may be an enzyme belonging to the enzyme classes polygalacturonases (EC3.2.1.15), pectinesterases (EC3.2.1.11), pectin lyases (EC4.2.2.10) and hemicellulases such as endo-1,3-b-xylosidase (EC 3.2.1.32), xylan 1,4-b-xylosidase (EC 3.2.1.37) and a-L-arabinofuranosidase (EC 3.2.1.55). A suitable source organism for pectinases may be *Aspergillus niger*.

In a preferred embodiment, the cleaning composition comprises a hydrolytic enzyme composition produced by a strain of the fungus *Aspergillus aculeatus*, preferably *Aspergillus aculeatus*, CBS 101.43. It is known that this strain produces an enzyme composition comprising pectolytic and a range of hemicellulolytic enzyme activities.

The hydrolase(s) are present in the cleaning composition in an amount from about 0.01 to about 5000 $\mu$g protein/ml of composition, preferably from about 1 to about 500 $\mu$g protein/ml of composition.

The term "oxidoreductase", as used herein, denotes an enzyme classified as EC 1. according to the Enzyme Nomenclature (1992), i.e. any enzyme classified as EC 1.1 (acting on the CH—OH group of donors), EC 1.2 (acting on the aldehyde or oxo group of donors), EC 1.3 (acting on the CH—CH group of donors), EC 1.4 (acting on the CH—NH$_2$ group of donors), EC 1.5 (acting on the CH—NH group of donors), EC 1.6 (acting on NADH or NADPH), EC 1.7 (acting on other nitrogenous compounds as donors), EC 1.8

(acting on a sulfur group of donors), EC 1.9 (acting on a heme group of donors), EC 1.10 (acting on diphenols and related substances as donors), EC 1.11 (acting on a peroxide as acceptor), EC 1.12 (acting on hydrogen as donor), EC 1.13 (acting on single donors with incorporation of molecular oxygen (oxygenases), EC 1.14 (acting on paired donors with incorporation of molecular oxygen), EC 1.15 (acting on superoxide radicals as acceptor), EC 1.16 (oxidizing metal ions), EC 1.17 (acting on —CH$_2$— groups), EC 1.18 (acting on reduced ferredoxin as donor), EC 1.19 (acting on reduced flavodoxin as donor), and EC 1.97 (other oxidoreductases).

Preferably, the oxidoreductase to be used according to the invenion is selected from the group consisting of oxidases, peroxidases and laccases, preferably from glucose oxidases, amino acid oxidases, xanthine oxidases, ascorbic acid oxidases, lacto-peroxidases, horseradish peroxidases, myeloperoxidases, laccases, Coprinus peroxidases, and haloperoxidases.

Laccases are enzymes that catalyze the oxidation of a substrate with oxygen; they are known from microbial, plant and animal origins. More specifically, laccases (EC 1.10.3.2) are oxidoreductases that function with molecular oxygen as electron acceptor. Molecular oxygen from the atmosphere will usually be present in sufficient quantity, so normally it is not necessary to add extra oxygen to the process medium. Examples of a laccase enzyme useful in the compositions of the present invention is laccase obtainable from the strain *Coprinus cinereus*, IFO 30116, or from a laccase having immunochemical properties identical to those of a laccase derived from *Coprinus cinereus*, IFO 30116; or obtainable from a strain of *Myceliophthora thermophila* as disclosed in WO 91/05839.

A useful peroxidase is preferably producible by plants (e.g. horseradish or soybean peroxidase) or microorganisms such as fungi or bacteria. Some preferred fungi include strains belonging to the subdivision Deuteromycotina, class Hyphomycetes, e.g. Fusarium, Humicola, Tricoderma, Myrothecium, Verticillum, Arthromyces, Caldariomyces, Ulocladium, Embellisia, Cladosporium or Dreschlera, in particular Fusarium oxysporum (DSM 2672), *Humicola insolens, Trichoderma resii, Myrothecium verrucaria* (IFO 6113), *Verticillum alboatrum, Verticillum dahlie, Arthromyces ramosus* (FERM P-7754), *Caldariomyces fumago, Ulocladium chartarum, Embellisia alli* or *Dreschlera halodes*. Other preferred fungi include strains belonging to the subdivision Basidiomycotina, class Basidiomycetes, e.g. Coprinus, Phanerochaete, Coriolus or Trametes, in particular *Coprinus cinereus f. microsporus* (IFO 8371), *Coprinus macrorhizus, Phanerochaete chrysosporium* (e.g. NA-12) or Trametes (previously called Polyporus), e.g. *T. versicolor* (e.g. PR4 28-A). Further preferred fungi include strains belonging to the subdivision Zygomycotina, class Mycoraceae, e.g. Rhizopus or Mucor, in particular *Mucor hiemalis*.

Some preferred bacteria include strains of the order Actinomycetales, e.g. *Streptomyces spheroides* (ATTC 23965), *Streptomyces thermoviolaceus* (IFO 12382) or *Streptoverticillum verticillium* ssp. *verticillium*. Other preferred bacteria include *Bacillus pumilus* (ATCC 12905), *Bacillus stearothermophilus, Rhodobacter sphaeroides, Rhodomonas palustri, Streptococcus lactis, Pseudomonas purrocinia* (ATCC 15958) or *Pseudomonas fluorescens* (NRRL B-11). Further preferred bacteria include strains belonging to Myxococcus, e.g. *M. virescens*.

In the context of this invention, compounds possessing peroxidase activity comprise peroxidase enzymes and peroxidase active fragments derived from cytochromes, haemoglobin or peroxidase enzymes, and synthetic or semisynthetic derivatives thereof, e.g., iron porphyrins, and iron phthalocyanine and derivatives thereof.

Generally, the enzymes to be used in the method of the invention may be monocomponent (recombinant) enzymes i.e. enzymes essentially free from other proteins or enzyme proteins. A recombinant enzyme may be cloned and expressed according to standard techniques conventional to the skilled person. However, the enzyme may also be used in the form of an enzyme preparation optionally enriched in an enzyme exhibiting the desired enzyme activity as the major enzymatic component, e.g. a mono-component enzyme preparation.

Particularly, a recombinantly produced peroxidase is a peroxidase derived from a Coprinus sp., in particular *C. macrorhizus* or *C. cinereus* according to WO 92/16634, or a variant thereof, e.g., a variant as described in WO 94/12621. However, the peroxidase may also by produced by conventional fermentation of a strain belonging to the genus Coprinus, preferably the species *Coprinus cinereus* or *Coprinus mactorhizus*, more preferably *Coprinus cinereus*, IFO 8371 or IFO 30114.

In combination with a peroxidase, it is preferred to use an enhancing agent capable of acting as an electron-donor. Useful examples of such enhancing agents are described below.

A. A source of ionic iodide which may be enzymatically converted to iodine when contacted with peroxidase enzyme in an aqueous solution for a time and under conditions sufficient to permit the conversion. In the present context, a preferred source of ionic iodide is a water-soluble iodide salt such as an alkaline metal iodide salt, e.g. potassium iodide (KI), sodium iodide (NaI), or lithium iodide, ammonium iodide, calcium iodide. Sodium iodide and potassium iodide are preferred.

B. Another preferred enhancing agent is a source of the thiocyanate ion (SCN$^-$), e.g. sodium thiocyanate, potassium thiocyanate, ammonium thiocyanate, and other thiocyanate salts, preferably sodium thiocyanate and potassium thiocyanate.

C. Another useful enhancing agent is the compound described by the following formula:

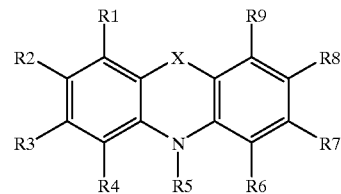

in which formula X represents (—O—) or (—S—), and the substituent groups $R^1$–$R^9$, which may be identical or different, independently represents any of the following radicals: hydrogen, halogen, hydroxy, formyl, carboxy, and esters and salts hereof, carbamoyl, sulfo, and esters and salts hereof, sulfamoyl, nitro, amino, phenyl, $C_1$–$C_{14}$-alkyl, $C_1$–$C_5$-alkoxy, carbonyl-$C_1$–$C_5$-alkyl, aryl-$C_1$–$C_5$-alkyl; which carbamoyl, sulfamoyl, and amino groups may furthermore be unsubstituted or substituted once or twice with a substituent group $R^{10}$; and which phenyl may furthermore be unsubstituted or substituted with one or more substituent groups $R^{10}$; and which $C_1$–$C_{14}$-alkyl, $C_1$–$C_5$-alkoxy, carbonyl-$C_1$–$C_5$-alkyl, and aryl-$C_1$–$C_5$-alkyl groups may be saturated or unsaturated, branched or unbranched, and may furthermore be unsubstituted or substituted with one or more substituent groups $R^{10}$;

which substituent group R represents any of the following radicals: halogen, hydroxy, formyl, carboxy and esters and salts hereof, carbamoyl, sulfo and esters and salts hereof, sulfamoyl, nitro, amino, phenyl, aminoalkyl, piperidino, piperazinyl, pyrrolidin-1-yl, $C_1$–$C_5$-alkyl, $C_1$–$C_5$-alkoxy; which carbamoyl, sulfamoyl, and amino groups may furthermore be unsubstituted or substituted once or twice with hydroxy, $C_1$–$C_5$-alkyl, $C_1$–$C_5$-alkoxy; and which phenyl may furthermore be substituted with one or more of the following radicals: halogen, hydroxy, amino, formyl, carboxy and esters and salts hereof, carbamoyl, sulfo and esters and salts hereof, and sulfamoyl; and which $C_1$–$C_5$-alkyl, and $C_1$–$C_5$-alkoxy groups may furthermore be saturated or unsaturated, branched or unbranched, and may furthermore be substituted once or twice with any of the following radicals: halogen, hydroxy, amino, formyl, carboxy and esters and salts hereof, carbamoyl, sulfo and esters and salts hereof, and sulfamoyl;

or in which general formula two of the substituent groups $R^1$–$R^9$ may together form a group —B—, in which B represents any of the following the groups: (—$CHR^{10}$—N═N—), (—CH═CH—)$_n$, (—CH═N—)$_n$ or (—N═$CR^{10}$—$NR^{11}$—), in which groups n-represents an integer of from 1 to 3, $R^{10}$ is a substituent group as defined above and $R^{11}$ is defined as $R^{10}$. (It is to be understood that if the above mentioned formula comprises two or more $R^{10}$-substituent groups, these $R^{10}$-substituent groups may be the same or different).

In particular embodiments, the enhancing agent is 10-methylphenothiazine, phenothiazine-10-propionic acid, N-hydroxysuccinimide phenothiazine-10-propionate, 10-ethyl-phenothiazine-4-carboxylic acid, 10-ethylphenothiazine, 10-propylphenothiazine, 10-isopropylphenothiazine, methyl phenothiazine-10-propionate, 10-phenylphenothiazine, 10-allylphenothiazine, 10-(3-(4-methylpiperazin-1-yl)propyl)phenothiazine, 10-(2-pyrrolidin-1-yl-ethyl)phenothiazine, 2-methoxy-10-methylphenothiazine, 1-methoxy-10-methylphenothiazine, 3-methoxy-10-methylphenothiazine, 3,10-dimethylphenothiazine, 3,7,10-trimethylphenothiazine, 10-(2-hydroxyethyl)phenothiazine, 10-(3-hydroxypropyl)phenothiazine, 3-(2-hydroxyethyl)-10-methylphenothiazine, 3-hydroxymethyl-10-methylphenothiazine, 3,7-dibromophenothiazine-10-propionic acid, phenothiazine-10-propionamide, chlorpromazine, 2-chloro-10-methylphenothiazine, 2-acetyl-10-methylphenothiazine, 10-methylphenoxazine, 10 -ethylphenoxazine, phenoxazine-10-propionic acid, 10-(2-hydroxyethyl)phenoxazine or 4-carboxyphenoxazine-10-propionic acid.

D. Another example of a useful enhancing agent is a compound described by the following formula:

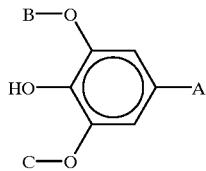

in which formula A is a group such as —D, —CH═CH—D, —CH═CH—CH═CH—D, —CH═N—D, —N═N—D, or —N═CH—D, in which D is selected from the group consisting of —CO—E, —$SO_2$—E, —N—XY, and —$N^+$—XYZ, in which E may be —H, —OH, —R, or —OR, and X and Y and Z may be identical or different and selected from —H and —R; R being a $C_1$–$C_{16}$ alkyl, preferably a $C_1$–$C_8$ alkyl, which alkyl may be saturated or unsaturated, branched or unbranched and optionally substituted with a carboxy, sulfo or amino group; and B and C may be the same or different and selected from $C_mH_{2m+1}$; $1 \leq m \leq 5$.

In a preferred embodiment A in the above mentioned formula is —CO—E, in which E may be —H, —OH, —R, or —OR; R being a $C_1$–$C_{16}$ alkyl, preferably a $C_1$–$C_8$ alkyl, which alkyl may be saturated or unsaturated, branched or unbranched and optionally substituted with a carboxy, sulfo or amino group; and B and C may be the same or different and selected from $C_mH_{2m+1}$; $1 \leq m \leq 5$.

In the above mentioned formula A may be placed meta to the hydroxy group instead of being placed in the paraposition as shown.

In particular embodiments, the enhancing agent is acetosyringone, methylsyringate, ethylsyringate, propylsyringate, butylsyringate, hexylsyringate, or octylsyringate.

E. Yet another useful enhancing agent is an azino compound described by the general formula

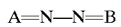

in which formula the symbols A and B, which may be identical or different, independently represents any of the substituents II, III, IV, and V, presented in FIG. 2;

in which substituents the symbols X and Y, which may be identical or different, independently represents carbon, nitrogen, which nitrogen may be unsubstituted or substituted with a substituent group $R^5$, sulfur, oxygen, selenium or tellurium; and in which substituents the substituent groups $R^1$, $R^2$, $R^3$, and $R^4$, which may be identical or different, independently represents hydrogen, halogen, a hydroxy group, a $C_1$–$C_3$ alkoxy group, a formyl group, a carboxy group, a sulfo group, a nitro group, a $C_1$–$C_5$ alkyl group, which alkyl group may furthermore be saturated or unsaturated, linear or branched, or an amino group, which amino group may furthermore be unsubstituted or substituted once or twice with a substituent group $R^5$;

which substituent group $R^5$ represents halogen, a hydroxy group, a $C_1$–$C_3$ alkoxy group, a $C_1$–$C_5$ alkyl group, or an amino group. The peroxidase enhancing agent may be in free form or in the form of an addition salt.

In preferred embodiments, the substituent groups $R^1$, $R^2$, $R^3$, and $R^4$, which may be identical or different, independently represents hydrogen, halogen, a hydroxy group, a $C_1$–$C_3$ alkyl group, or a sulfo group. Preferably, the halogen is fluoro, chloro, or bromo. Preferably, the $C_1$–$C_3$ alkyl group is methyl, ethyl, propyl, or isopropyl.

In preferred embodiments, the substituent group $R^5$ represents halogen, a hydroxy group, a $C_1$–$C_3$ alkoxy group, a $C_1$–$C_3$ alkyl group, or an amino group.

In a most preferred embodiment, a peroxidase enhancing agent of the invention is 2,2'-azino-bis(3-ethylbenzothiazoline-6-sulfonate). This compound, abbreviated ABTS, is a chromogenic substrate, and a common peroxidase and phenol oxidase assay agent.

It has, moreover, been demonstrated that ABTS, contrary to the enhancers known and described above, is capable of acting as a peroxidase enhancing agent at highly alkaline conditions, i.e. above pH 9. This feature allows ABTS to be implemented into e.g. detergent compositions, intended for performance in the range pH 7–13, particularly the range pH 8–12, preferably the range pH 9–11.

The enhancing agent may be present in the antimicrobial composition in concentrations corresponding to from 0.005 to 1000 mmole per g of substrate (microbial cells, biomass), preferably 0.05 to 500 mmole per g of substrate, more preferably 0.5 to 100 mmole per g of substrate.

Without being limited to any theory it is presently contemplated that there is a positive correlation between the half-life of the radical which the enhancing agent forms in the relevant aqueous medium and its efficiency, and that this half-life is significantly longer than the half-life of any of the substances selected from the group consisting of p-hydroxycinnamic acid, 2,4-dichlorophenol, p-hydroxybenzene sulphonate, vanillin and p-hydroxybenzoic acid (i.e. the enhancing agents disclosed in WO 92/18683).

As the half-life of the radical is dependent on, inter alia, the pH, the temperature and the buffer of the aqueous medium, it is very important that all these factors are the same when the half-lifes of the radicals of various enhancing agents are compared.

Preferably, the amount of oxidoreductase in the disinfecting composition of the present invention is from about 0.01 to about 1000 µg protein/ml of composition, more preferably from about 10 to about 100 µg protein/ml of composition. In case of oxidases and peroxidases, the preferred amount is from about 0.01 to about 100 oxidase or peroxidase units (e.g. GODU or PODU) per ml of composition, more preferably from about 0.1 to about 50 units/ml.

Definition of enzyme units 1 glucose oxidase unit (GODU) is the amount of enzyme which, under standard conditions (i.e. pH 5.6, 30° C., 20 min. incubation time, acetate buffer, and glucose 16.2 g/l, 90 mM, as substrate) forms 1 mmol of hydrogen peroxide per minute. A folder AF 266/1 describing this analytical method is available upon request to Novo Nordisk A/S, Denmark, which folder is hereby included by reference.

1 peroxidase unit (PODU) is the amount of enzyme that catalyzes the conversion of 1 mmole hydrogen peroxide per minute at the following analytical conditions: 0.88 mM hydrogen peroxide, 1.67 mM 2,2'-azinobis(3-ethylbenzothiazoline-6-sulfonate), 0.1 M phosphate buffer, pH 7.0, incubated at 30° C., photometrically followed at 418 nm.

1 pectinase unit (PSU) is the amount of enzyme that reduces the viscosity of a solution of pectic acid. The activity is measured relative to a known standard of 75000 PSU/g at the following analytical conditions: acetate buffer, 40° C., pH 4.0, 1.43% pectic acid and 30 min. reaction time.

1 lactoperoxidase unit (LP) will form 1.0 mg of purpurogallin from pyrogallol in 20 sec. at pH 6.0 at 20° C. Standard assay from Sigma Chemical Company.

The composition

The enzymatic composition according to the invention may be a cleaning composition, i.e. comprising one or more hydrolases capable of removing or releasing biofilm from a surface, a disinfecting composition, i.e. comprising an oxidoreductase capable of killing living microbial, preferably bacterial, cells present in a biofilm, or a combination thereof, i.e. a composition comprising at least a hydrolase and an oxidoreductase in amounts efficient for cleaning and disinfecting a surface fully or partly covered by a biofilm.

The composition of the invention further comprises a conventional surfactant.

The process

The method of the invention is preferably carried out at a pH or in a pH range at which the applied enzymes are active, for example within a pH range wherein the actual enzymes have at least about 50% relative activity, more preferably at least about 80% activity. Accordingly, it is preferred that pH of the cleaning and/or disinfecting composition is in the range of 4.5–11, preferably 5–9, more preferably 5.5–7.5.

The method of the invention is preferably carried out at a temperature or in a temperature range at which the applied enzymes are active, for example within a temperature range wherein the actual enzymes have at least about 50% relative activity, more preferably at least about 80% activity. Typically, the method of the invention is carried out at a temperature (of the cleaning and/or disinfecting composition) in the range of 10–60° C., preferably 20–50° C., more preferably 25–40° C.

The following example illustrates the invention.

EXAMPLE 1

Biofilms were grown in a model system using *Pseudomonas aeruginosa* ATCC 10148, *Pseudomonas fluorescens* strain AH2 (Gram et al. 1990), *Staphylococcus epidermidis* DMS 20042 and *Staphylococcus aureus* ATCC 25923. Tryptone Soya Broth (TSB) from Oxoid CM131 was used as growth medium.

Stainless steel type AISI 304 with a #4 finish (polish grain 180) was cut into 12*20 mm discs. Polypropylene discs (12*20 mm; Ral. 7032, Dukadan A/S) were cleaned by scrubbing in a neutral detergent (Triton) and then rinsed in water before autoclaving. The discs were cleaned in water followed by chloroform, methanol and finally acetone (5 min each) before sterilisation by autoclaving at 121° C. for 20 min prior to use.

Biofilm development

Sterile steel or polypropylene discs were clamped vertically in a sterile steel rack in a beaker. The rack holds up to 20 discs in an arrangement which allows the free circulation of liquid when immersed in culture medium. *S. aureus, P. aeruginosa* and *P. fluorescens* were precultured in TSB for 24 h at 26° C.

*S. epidermidis* was precultured in TSB for 24 h at 30° C. Staphylococcus spp. were inoculated in TSB and Pseudomonas spp. were inoculated (approximately 103 cfu/ml) in TSB diluted 1:5 with sterile water. The inoculated media was poured into the beaker covering the discs and a biofilm was allowed to develop on both sides of the discs at 26° C. (*S. epidermidis* at 30° C.) over 4 days at slight stirring (200 rpm).

All discs were aseptically rinsed for 1 minute in sterile phosphate buffer (0.067 M, pH 7) to remove planktonic cells before incubation with enzymes.

Antibacterial enzymes

Glucose oxidase (Novo Nordisk A/S) was used with 3 g/L D(+)-glucose (Sigma G-7528) as electron donor and oxygen as the electron acceptor being reduced to hydrogen peroxide.

Lactoperoxidase (Sigma Chemicals Co.) was used with hydrogen peroxide as electron acceptor and 2 mM thiocyanate as electron donor.

Pectinase produced by fermentation of a strain of *Aspergillus aculeatus* (Novo Nordisk) is a commercially available multicomponent enzyme preparation containing protease activity and a wide range of carbohydrases including pectinase, arabanase, cellulase, hemi-cellulase, β-glucanase and xylanase activities.

Enzymatic removal and killing of biofilm cells

Enzymes were diluted in phosphate buffer (pH 7), filter sterilized and added to the buffer containing the biofilm discs. Steel and polypropylene discs were incubated with enzymes at 20° C. for 15 min without agitation. For both substrata, sterile buffer with no enzymes added was used as control. After enzyme treatment the substrata were gently rinsed once in sterile buffer followed by staining prior to microscopy or enumeration by conductance measurements.

The bactericidal activity of glucose oxidase and lactoperoxidase was also determined on planktonic cells of *S. aureus, S. epidermidis, P. aeruginosa* and *P. fluorescens*.

Planktonic cells from the biofilm development were diluted 1:9 in 0.067 M phosphate buffer (pH 7.0) and mixed with glucose oxidase (0, 5 or 10 GODU/ml) and lactoperoxidase (0, 1 or 5 U/ml) at 20° C. for 15 min. Bactericidal activity against planktonic cells was estimated by inoculation of 0.1 ml from the cells suspensions to Malthus cells.
Estimation of biofilm Fluorescence microscopy: The tetrazolium salt 5-cyano-2, 3-ditolyl tetrazolium chloride (CTC)(Polysciences, Inc., Warrington, Pa.) was dissolved in distilled filter sterilised water (10 mM). CTC was used as an indicator of cellular viability, as the aqueous solution of CTC is nearly colourless and nonfluorescent, while the corresponding formazan product fluoresces in the red range at approximately 620 nm when excited at 420 nm. The DNA-binding fluorochrome DAPI (4',6-diamidino-2-phenylindole, Sigma D-9542) was used as an indicator for the total cell number, and the biofilm cells were stained with DAPI after CTC straining to allow enumeration of total and respiring cells within the same preparation (30).

The discs with biofilm were after enzyme treatment incubated in the dark for 45 min (20° C.) with 0.5 ml Tryptose Phosphate Broth (TPB) and CTC-tetrazolium salt (12.5 mM). During the last 5 min of the CTC straining, DAPI (3 mM) was added. The stained cells were examined with the ×100 oil immersion fluorescence objective on an Olympus model BX50 microscope equipped with a 200 W mercury burner. The filter combination used for viewing CTC-stained cells was a 480–550 nm excitation filter and a 590 nm barrier filter (Olympus cube model U-MSWG). DAPI stained cells were viewed with a 330–385 nm excitation filter and a 420 barrier filter (Olympus cube model U-MWU).

Conductance measurements: Indirect Malthus measurements were used when enumerating adherent cells on the substrata (Johnston & Jones, 1995). The discs were after incubation with enzymes rinsed in the same buffer as used for the enzyme treatment and transferred to Malthus tubes containing 3 ml of growth media in the outer tube and 0.5 ml 0.1 M KOH in the inner tube (Dezenclos et al. 1994). TSB was used as growth media for detection of P. aeruginosa and P. fluorescens, whereas BHI was used for detection of S. aureus and Strep. mutans. Tubes were placed in a Malthus 2000 (Malthus Flexi 2000, Malthus Instrument Limited) and incubated at 37° C., except samples with P. fluorescens which were incubated at 25° C.

Carbondioxide produced by the bacteria will be absorbed by the KOH and thereby altering the conductivity. Changes in conductance were plotted against time and the detection time (DT) was determined as the time taken from start of the measurement until a rapid change in conductance was detecable by the Malthus. The DT can be related to the number of cells present at the start of the test by use of a calibration curve, which was constructed for each organism by inoculating Malthus tubes with a tenfold dilution series (Johansen et al. 1995).

Results

The estimation of exact number of living cells on the substrata was in all experiments determined by conductance measurements. But by the Malthus method it is not possible to distinguish between a bactericidal activity of the enzymes or an enzymatic removal of biofilm. Therefore a decrease in living bacteria on the substrata has to be compared with the simultaneously removal of biofilm from the substrata which was estimated by the DAPI/CTC staining.

Pectinase the number of bacterial cells in biofilms on stainless steel (Table 1). The activity of Pectinase was observed as a removal of biofilm without any significant bactericidal activity against neither of the four strains, determined by the combined DAPI/CTC staining.

Table 1: Reduction in biofilm on stainless steel after treatment with pectinex ultra SP for 15 min at 20° C. (pH 7).

| Pectinase | Biofilm reduction (%) | | | |
|---|---|---|---|---|
| (PSU/ml) | S. aureus | S. epidermidis | P. aeruginosa | P. fluorescens |
| 0 | — | — | — | — |
| 0.18 | 83 | 39 | 0 | 0 |
| 1.8 | 98 | 45 | 92 | 36 |
| 18 | 98 | 93 | 95 | 50 |
| 180 | 99.1 | 95 | 95 | 82 |
| 1800 | 99.7 | 97 | 95 | 85 |

All cells stainable by DAPI were also stained with CTC indicating that all visible cells were respiring. After treatment with Pectinase the DAPI staining clearly showed a removal of P. aeruginosa biofilm from the surface and the CTC staining showed the remaining cells to be respiring which indicate no bactericidal activity of Pectinase.

In general, S. aureus and S. epidermidis biofilms were more sensitive to enzymatic removal by Pectinase than P. aeruginosa and P. fluorescens biofilms (Table 1). S. aureus biofilm was most sensitive to Pectinase, as 0.18 PSU Pectinase per ml removed 83% of the biofilm. P. fluorescens was the most resistant biofilm, as 1800 PSU Pectinase per ml was needed to removed 85% of the biofilm. The removal of biofilm on polypropylene by Pectinase was similar to the removal of biofilm on stainless steel.

The combination of glucoseoxidase and lactoperoxidase significantly lowered the counts of actively respiring cells and reduced the number of living cells in the four tested biofilms (Table 2 and 3). The viability of Staphylococcus biofilm was reduced 1 to 2 log units when exposed to glucose oxidase (10 GODU/ml) and lactoperoxidase (5 U/ml) whereas the viability of Pseudomonas biofilm was reduced more than 3 log units. The extent of killing was, however, lower than that obtained when planktonic suspensions of cells had been exposed, as planktonic cells of Pseudomonas spp. were reduced approximately 5 log units when exposed to glucose oxidase (10 GODU/ml) and lactoperoxidase (5 U/ml)(Table 2).

Table 2: Bactericidal activity against Pseudomonas aeruginosa and Pseudomonas fluorescens cells in biofilm on stainless steel and planktonic cells caused by glucose oxidase and lactoperoxidase after treatment for 15 min at 20° C. The cell concentration before enzyme treatment is given and bactericidal activity is shown relative to cell numbers of untreated samples

| | | Bactericidal activity ($Log_{10}$ reduction) | | | |
|---|---|---|---|---|---|
| | | P. aeruginosa | | P. fluorescens | |
| GOD (U/ml) | LP (U/ml) | biofilm cells $1.7*10^8$ cfu/disc | planktonic cells $2.3*10^8$ cfu/ml | biofilm cells $1.9*10^8$ cfu/disc | planktonic cells $8.0*10^8$ cfu/ml |
| 0 | 0 | — | — | — | — |
| 0 | 1 | 0.0 | 0.8 | 0.1 | 0.9 |
| 0 | 5 | 0.0 | 1.1 | 0.9 | 1.1 |
| 5 | 0 | 0.0 | 0.0 | 0.8 | 0.1 |
| 5 | 1 | 1.5 | 2.5 | 2.2 | 2.7 |

-continued

| GOD (U/ml) | LP (U/ml) | BacTericidal activity (Log₁₀ reduction) | | | |
|---|---|---|---|---|---|
| | | P. aeruginosa | | P. fluorescens | |
| | | biofilm cells 1.7*10⁸ cfu/disc | planktonic cells 2.3*10⁸ cfu/ml | biofilm cells 1.9*10⁸ cfu/disc | planktonic cells 8.0*10⁸ cfu/ml |
| 5 | 5 | 1.7 | 3.4 | 2.5 | 4.0 |
| 10 | 0 | 0.3 | 0.0 | 2.4 | 0.2 |
| 10 | 1 | 3.0 | 2.7 | 3.0 | 3.0 |
| 10 | 5 | 3.0 | 3.5 | 3.0 | 4.5 |

Planktonic cells of *S. aureus* was comparable to biofilm cells in sensitivity to oxidoreductases, thus *S. aureus* was reduced approximately 2–3 log units when exposed to glucose oxidase (10 GODU/ml) and lactoperoxidase (5 U/ml)(Table 3). Planktonic cells of *S. epidermidis* were significantly more sensitive to oxidoreductases than the biofilm cells as the number of viable planktonic cells decreased approximately 5 log units compared to a reduction of 1 log unit in the number of biofilm cells. However, the concentration of viable cells in the *S. epidermidis* biofilm was approximately $10^7$ cfu/disc whereas the concentration of planktonic cells was approximately $10^6$ cfu/ml, therefore the ratio between cell number and concentration of the oxidoreductases was different for biofilm and planktonic cells of *S. epidermidis*, respectively (Table 3).

Table 3: Bactericidal activity against *Staphylococcus aureus* and *S. epidermidis* cells in biofilm on stainless steel and planktonic cells caused by glucose oxidase and lactoperoxidase after treatment for 15 min at 20° C. The cell concentration before enzyme treatment is given and bactericidal activity is shown relative to cell numbers of untreated samples

| GOD (U/ml) | LP (U/ml) | Bactericidal activity (Log₁₀ reduction) | | | |
|---|---|---|---|---|---|
| | | S. aureus | | S. epidermidis | |
| | | biofilm cells 3.1*10⁷ cfu/disc | planktonic cells 7.0*10⁷ cfu/ml | biofilm cells 3.6*10⁷ cfu/disc | planktonic cells 2.2*10⁶ cfu/ml |
| 0 | 0 | — | — | — | — |
| 0 | 1 | 0.0 | 0.0 | 0.2 | 0.0 |
| 0 | 5 | 0.0 | 0.0 | 0.4 | 0.3 |
| 5 | 0 | 0.0 | 0.0 | 0.3 | 0.6 |
| 5 | 1 | 0.5 | 0.4 | 0.9 | 0.8 |
| 5 | 5 | 0.7 | 1.0 | 1.2 | 2.3 |
| 10 | 0 | 0.0 | 0.1 | 0.2 | 1.2 |
| 10 | 1 | 2.0 | 2.3 | 1.2 | 4.0 |
| 10 | 5 | 2.0 | 2.7 | 1.4 | 5.0 |

There was no significant difference in the bactericidal activity of the oxidoreductase system towards biofilm on stainless steel compared to biofilm on polypropylene except for *P. aeruginosa* biofilm on polypropylene where glucose oxidase (5 GODU/ml) combined with lactoperoxidase (5 U/ml) killed 99.99% of the biofilm cells compared to 98% of the *P. aeruginosa* biofilm on stainless steel.

The complex mixture of polysaccharide hydrolysing enzymes in Pectinex ultra was able to remove a model bacterial biofilm on stainless steel but showed no significant bactericidal activity. By contrast, oxidoreductases were bactericidal against biofilm cells, but caused no removal of the biofilm. Furthermore, the combination of oxidoreductases and polysaccharide hydrolysing enzymes was bactericidal and removed the biofilm.

The combination of glucose oxidase with lactoperoxidase was bactericidal against biofilm cells, however, the bactericidal activity of the oxidoreductase system was less severe against biofilm cells compared to its effect on planktonic cells. It is a well known phenomenon that biofilm cells are more resistant than planktonic cells (Brown et al. 1995, Khardori et al. 1995)). The diffusion of thiocyanate and hydrogenperoxide into the biofilm will decrease the susceptibility of biofilm cells compared to planktonic cells suggesting that the underlying cells in the biofilm will escape the bactericidal activity of the oxidoreductases unless the biofilm cells are released from the surface. This may explain the small difference in susceptibility of Staphylococcus biofilm and planktonic cells, respectively, as the thin biofilms of Staphylococcus spp. will have a limited protection of the biofilm cells compared to the thick biofilms of Pseudomonas spp. Therefore the bactericidal activity of oxidoreductases can be improved by using a combination of biofilm degrading enzymes together with the oxidoreductase system.

REFERENCES

Brown, M. L., H. C. Aldrich and J. J. Gauthier. 1995. Relationship between glycocalyx and providone-iodine resistance in *Pseudomonas aeruginosa* (ATCC 27853) biofilms. Appl. Environ. Microbiol. 61:187–193.

Dezenclos, T., M. Ascon-Cabrera, D. Ascon, J. -M. Lebeault and A. Pauss. 1994. Optimisation of the indirect impedancemetry technique; a handy technique for microbial growth measurements. Appl. Microbiol. Biotechnol. 42:232–238.

Gram, L., C. Wedell-Nedergaard and H. H. Huss. 1990. The bacteriology of fresh and spoiling Lake Victorian Nile perch (*Lates niloticus*). Int. J. Food Microbiol. 10:303–316.

Johansen, C., T. Gill and L. Gram. 1995. Antibacterial effect of protamine assayed by impedimetry. J. Appl. Bacteriol. 78:297–303.

Johnston, M. and M. V. Jones. 1995. Disinfection tests with intact biofilms: combined use of the modified Robbins Device with impedance detection. J. Microbiol. Methods 21:15–26.

Khardori, N., M. Yassien and K. Wilson. 1995. Tolerance of *Staphylococcus epidermidis* grown from indwelling vascular catheters to antimicrobial agents. J. Industial Microbiol. 15:148–151.

What is claimed is:

1. A method for cleaning and disinfecting a surface at least partially covered by a biofilm layer, the method comprising contacting the biofilm, sequentially or simultaneously, with:

(a) a cleaning composition comprising one or more hydrolases in an amount effective for at least partially releasing the biofilm layer from the surface; and (b) a disinfecting composition comprising (i) a laccase at a concentration between about 0.01 to about 1000 mg protein/ml composition and (ii) an oxidation enhancer, wherein said enhancer has the formula

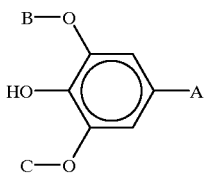

wherein
- (i) A is selected from the group consisting of —CO—D and —SO$_2$—D, wherein D is —H, —OH, —R, or —OR; R being a C$_1$–C$_{16}$ alkyl; and
- (ii) B and C are the same or different and have the formula C$_m$H$_{2m+1}$, wherein $1 \leq m \leq 5$.

2. The method of claim 1, wherein the hydrolase is selected from the group consisting of cellulases, hemicellulases, pectinases, amylases, proteases, and lipases.

3. The method of claim 2, wherein the cellulases are selected from the group consisting of endoglucanases, cellobiohydrolases and β-glucosidases.

4. The method of claim 2, wherein the hemicellulases are selected from the group consisting of xylanases, mannanases, and xylan acetyl esterases.

5. The method of claim 2, wherein the pectinases are selected from the group consisting of arabinanases, α-arabino-furanosidases, galactanases, pectin lyases, pectin methyl esterases, polygalacturonases, rhamnogalacturonan acetyl esterases, and rhamnogalacturonases.

6. The method of claim 1, wherein the cleaning composition comprises a hydrolytic enzyme composition produced by a strain of the fungus *Aspergillus aculeatus*.

7. The method of claim 6, wherein the cleaning composition comprises a hydrolytic enzyme composition produced by a strain of the fungus *Aspergillus aculeatus*, CBS 101.43.

8. The method of claim 1, wherein the amount of hydrolase in the cleaning composition is from about 0.01 to about 5000 mg protein/ml of composition.

9. The method of claim 8, wherein the amount of hydrolase in the cleaning composition is from about 1 to about 500 mg protein/ml of composition.

10. The method of claim 1, wherein the amount of laccase in the disinfecting composition is from about 10 to about 100 mg protein/ml of composition.

11. The method of claim 1, wherein the pH of the cleaning and/or disinfecting composition is in the range of from 4.5 to 11.

12. The method of claim 11, wherein the pH of the cleaning and/or disinfecting composition is in the range of 5 to 9.

13. The method of claim 12, wherein the pH of the cleaning and/or disinfecting composition is in the range of from 5.5 to 7.5.

14. The method of claim 1, wherein the temperature of the cleaning and/or disinfecting composition is in the range of 10–60° C.

15. The method of claim 14, wherein the temperature of the cleaning and/or disinfecting composition is in the range of 20–50° C.

16. The method of claim 15, wherein the temperature of the cleaning and/or disinfecting composition is in the range of 25–40° C.

17. The method of claim 1, wherein the biofilm layer comprises living cells belonging to the genera Pseudomonas, Staphylococcus, or Aeromonas, or to the family Enterobacteriaceae.

18. The method of claim 1, wherein the enhancer is selected from the group consisting of methyl syringate, ethyl syringate, butyl syringate, lauryl syringate, syringaldehyde, and acetosyringon.

19. The method of claim 1, wherein the enhancer is methyl syringate.

* * * * *